United States Patent [19]
Cresson et al.

[11] Patent Number: 5,297,062
[45] Date of Patent: Mar. 22, 1994

[54] SENSOR, SYSTEM AND METHOD FOR DETERMINING Z-DIRECTIONAL PROPERTIES OF A SHEET

[75] Inventors: Thierry M. Cresson, Cupertino; John D. Goss; Barclay W. Wallace, both of San Jose, all of Calif.

[73] Assignee: Measurex Corporation, Cupertino, Calif.

[21] Appl. No.: 47,171

[22] Filed: Apr. 12, 1993

Related U.S. Application Data

[63] Continuation of Ser. No. 632,315, Dec. 21, 1990, abandoned.

[51] Int. Cl.⁵ ............................................. G01B 7/10
[52] U.S. Cl. ..................................... 364/564; 73/159; 162/198; 324/229
[58] Field of Search .................. 33/501.02; 73/159; 162/198; 250/360.1; 324/229; 364/563

[56] References Cited

U.S. PATENT DOCUMENTS

| | | | |
|---|---|---|---|
| 3,621,259 | 11/1971 | Boissevain | 250/360.1 |
| 3,828,248 | 8/1974 | Wennerberg | 73/159 X |
| 4,134,211 | 1/1979 | Typpo et al. | 33/501.02 |
| 4,866,984 | 9/1989 | Houghton | 73/159 |
| 4,901,445 | 2/1990 | Boissevain et al. | 33/501.02 |
| 5,104,488 | 4/1992 | Chase | 162/254 X |
| 5,132,619 | 7/1992 | Typpo | 73/159 X |
| 5,226,239 | 7/1993 | Boissevain et al. | 33/501.02 |
| 5,233,727 | 8/1993 | Boechler | 19/300 |

OTHER PUBLICATIONS

Hall: "On-Line Ultrasonic Measurement of Paper Strength"; Sensors; Jun. 1990; pp. 13, 14, 16, 18–20.

Primary Examiner—Edward R. Cosimano
Attorney, Agent, or Firm—Spensley Horn Jubas & Lubitz

[57] ABSTRACT

A sensor, system and method for determining the various Z-directional properties of a sheet by measuring the caliper of a moving sheet of material at a plurality of pressures. The invention employs a caliper gauge and a set of pressure transducers that can measure and send signals indicative of the caliper as well as pressures exerted on the sheet. The signals are then digitized by an analog-to-digital converter and sent to a computer. The computer uses the compressibility data to construct a compression stress-strain diagram where the slope of the curve in the linear region of the curve is defined as the compression modulus of elasticity which can be empirically correlated to the tensile modulus of elasticity for various grades of paper. The tensile modulus of elasticity can be then used in various formulas to determine other Z-directional physical properties of the sheet, such as tensile strength, extensional stiffness and Scott bonding.

32 Claims, 3 Drawing Sheets

SENSOR, SYSTEM AND METHOD FOR DETERMINING Z-DIRECTIONAL PROPERTIES OF A SHEET

This is a continuation of application Ser. No. 07/632,315 filed on Dec. 21, 1990, now abandoned.

BACKGROUND OF THE INVENTION

(1) Field of the Invention

The present invention relates to the field of sensors for measuring the properties of a sheet, and more particularly to a sensor and system including a caliper gauge for measuring sheet compressibility subjected to a plurality of pressures.

The invention uses the compressibility measurements to compute a compression modulus of elasticity which can be used to derive various Z-directional properties of the sheet, such as the tensile modulus of elasticity, the Z-directional tensile strength, extensional stiffness and Scott bonding.

(2) Description of the Related Art

Various types of caliper gauges are known in sensor technology and are used for measuring the thickness of rapidly moving sheet material. One type of caliper gauge is called a "contacting caliper gauge." Contacting caliper gauges typically have two opposing pads which are forced into contact with opposite sides of a sheet. The distance between the pads is measured and directly relates to the sheet thickness or "caliper."

It has been recognized that the aerodynamic design of the caliper pads must be considered if the pads are to be maintained on or near the sheet surface with relatively little external force. A previous caliper gauge having aerodynamically designed caliper pads is disclosed in the commonly assigned U.S. Pat. No. 4,901,445 to Mathew G. Boissevain, et al. This patent is incorporated herein by reference.

However, applicants are not aware of caliper gauges being used to simultaneously measure the compressibility of a sheet at a plurality of pressures or using such measurements to compute a compression modulus of elasticity which can be used to compute the tensile modulus of elasticity and to derive various Z-directional physical properties of the sheet, such as Z-directional tensile strength, extensional stiffness and Scott bonding.

One of the most critical properties involved in the manufacture of paper is its strength. Virtually all paper manufactured is sold with a strength specification of some sort, and acceptance of a manufacturer's paper depends on being able to meet this requirement. Paper strength has three basic orientations: 1) the machine direction, 2) the cross-direction, and 3) the Z-direction. The machine direction refers to the primary direction of sheet travel through the papermaking machinery. The cross-direction refers to the direction across the width of the sheet, in the plane of the sheet and perpendicular to the machine direction. The Z-direction extends perpendicular to the plane defined by the machine and cross-direction and is also referred to as the thickness direction.

A previous system for continuous determination of sheet strength in the cross-direction and machine direction is disclosed in the commonly assigned U.S. Pat. No. 4,866,984 to Paul J. Houghton which is incorporated by reference. This system does not, however, determine sheet strength in the Z-direction, and therefore does not provide a complete picture of paper strength. In addition, due to the alignment of wood fibers, which are the main constituent of paper, the strength for each orientation is substantially different.

The Z-directional strength of paper is usually given in terms of an empirical, destructive test. A common test is the Scott bond test where the Z-directional strength is determined by measuring the bonding between the different layers of fibers through the sheet. In the Scott bond test, a strip of paper or sample is delaminated by applying an in-plane shear force. One side of the sample is double-taped to a fixed support. The other side is taped to an "L" bracket. A pendulum is then released to hit the vertical side of the bracket and shear the sample. The energy lost in the delamination can be measured from the stopping position of the pendulum.

In another such destructive test, the Z-directional tensile test, a sample is delaminated by pulling on both surfaces in the Z-direction with an equal force. Double-sided tape is used on each side to transfer the stress to the sample. The paper strength is determined by measuring the force exerted on the paper when it ruptures.

Of course, neither test can be performed "on-line" as the paper is being manufactured in order to avoid the production of substandard material. Instead, the sample must be taken from the end of a reel after the reel has been completed. Since papermaking is a high speed continuous process, large amounts of paper can be easily produced before strength can be confirmed by a later measurement. The result of the time-consuming, off-line testing is that the strength measurement provided by perhaps several square feet must be accepted as representative of the thousands of square feet making up the reel. Consequently, it would be highly desirable to measure paper strength on-line while it is being manufactured.

An article by Hall, *On-Line ultrasonic Measurement of Paper Strength*, Sensors (1990), based on research at the Institute of Paper Science and Technology, describes the use of commercial fluid filled wheels which are adapted for out-of-plane ultrasound velocity measurements and caliper measurements for moving paper webs. However, no on-line data is presented and there is no apparent disclosure of how to correlate these measurements with Z-directional paper strength.

Nonetheless, Z-directional strength is important to monitor and control on-line, both to the efficiency of the paper mill and the efficiency of the processes in the converting operations. In a paper mill, there are several processes, such as those employing sizing presses and coaters, where highly viscous materials are applied to the paper. In the process of applying and drying these materials, the sheet or portions of the sheet can be pulled apart in the Z-direction, causing build-up on the applicators and dryers. In addition, there are other areas where either the surface of a calender roll or the surface of the sheet is dampened which causes the sheet to adhere to the roll.

However, too high a value of Z-directional strength can also cause problems. For example, if the Z-directional strength is obtained from too much densification of the sheet by wet pressing, or other means, then certain properties such as opacity, folding stiffness and tear strength will be reduced. Also, it can be generally stated that the higher the strength, the higher the cost of manufacturing the paper.

The company that buys the paper and converts it into a product has similar types of Z-directional strength requirements. Many of the converting operations, such as corrugators, printers, coaters and laminators, also apply substances of high viscosity that create a Z-directional force on the sheet of paper. Here again, if the Z-directional strength in the paper is too low, portions of the sheet will be pulled apart or delaminate in the Z-direction causing either sheet breaks or build-up on the applicator rolls or drying equipment.

Thus, it would be desirable to be able to obtain the Z-directional strength, as well as other Z-directional properties such as tensile strength, extensional stiffness and Scott bonding on-line to achieve the strength required by both the papermaker and the converter, while at the same time optimizing cost and manufacturing efficiency.

SUMMARY OF THE INVENTION

An object of the present invention is to provide a sensor, system and method for determining various Z-directional properties of a sheet by measuring the compressibility of the sheet subjected to a plurality of pressures. For example, the compressibility data can be used to compute the Z-directional compression modulus of elasticity. Such data also can be used to derive other Z-directional physical properties of the sheet, such as tensile strength, extensional stiffness and Scott bonding.

In one example of the invention, these and other objects are achieved by pressing a first and second major surface of a sheet on opposite sides at a plurality of pressures and measuring and sending signals indicative of the caliper of the sheet at each of these pressures to an analog-to-digital converter. The digitized signals are then sent to a computer which generates a stress-strain diagram. The ordinate of the diagram is the pressure or stress exerted upon the sheet. The abscissa of the diagram is the strain exerted on the sheet which is defined as the reduction in sheet thickness resulting from the difference in pressure divided by the thickness of the sheet at the lower pressure. From this data a Z-directional compression modulus of elasticity can be computed, which is defined as the slope of the stress-strain curve within the linear region of the curve. The Z-directional tensile modulus of elasticity can then be determined empirically. As stated earlier, such information can then be used to derive various other Z-directional properties of the sheet.

In another example of the invention, a system is provided for measuring a physical property of a moving sheet with a first and second major surface. A first sheet-contacting pad is disposed adjacent to the first major surface, while a second sheet-contacting pad opposing the first pad is disposed adjacent to the second major surface. A third sheet-contacting pad is disposed downstream from the first pad adjacent to the first major surface, while a fourth sheet-contacting pad opposing the third pad is disposed adjacent to the second major surface. Means operatively coupled to the first pad measure and generate a signal indicative of the distance between the first and second pads. Another means operatively coupled to the third pad measure and generate a signal indicative of the distance between the third and fourth pads. Means are provided for pressing the first and second pads against the sheet at a first pressure and the third and fourth pads at a second higher pressure. A transducer measures and generates signals indicative of these pressures. An analog-to-digital converter then digitizes the signals which are sent to a computer. The computer receives the digitized signals and converts them into compressibility data to construct a compression stress-strain diagram. The slope of the curve in the linear region is defined as the compression modulus of elasticity, which is empirically related to tensile modulus of elasticity which can then be used to derive various other Z-directional sheet properties.

BRIEF DESCRIPTION OF THE DRAWINGS

The foregoing objects, features and advantages of the invention will become more apparent from the following detailed description of the preferred embodiments taken in conjunction with the accompanying drawings, in which.

DESCRIPTION OF THE PREFERRED EMBODIMENTS

The following description is the best contemplated mode of carrying out the invention. This description is made for the purpose of illustrating the general principles of the invention and should not be taken in a limiting sense. The scope of the invention is best determined by reference to the appended claims. In the accompanying drawings, like numerals designate like parts.

Figure 1:
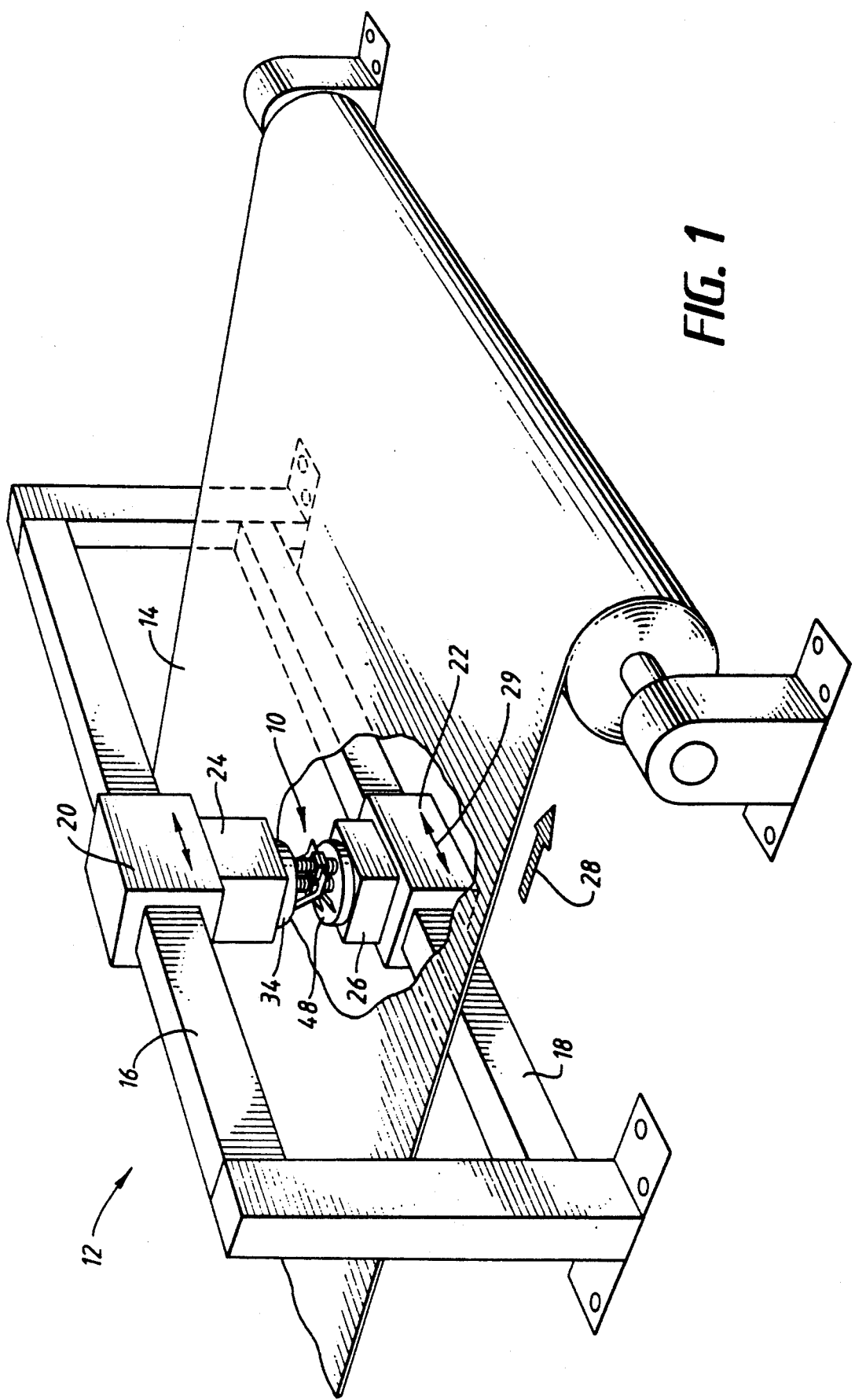
FIG. 1 is a simplified perspective view of a sheet scanner carrying a caliper gauge for measuring sheet compressibility immediately before the sheet is collected on a reel. Part of the sheet is removed to better illustrate the lower portion of the caliper gauge.

FIG. 1 illustrates one embodiment of a sheet thickness or caliper gauge 10 of the present invention carried by a scanner 12 which scans back and forth across a longitudinally moving paper sheet 14 being produced by a papermaking machine (not shown). The scanner 12 is of a conventional type, such as that described in the commonly assigned U.S. Pat. No. 3,621,259 to Mathew G. Boissevain. This patent is incorporated herein by reference.

The scanner 12 consists generally of a framework having a pair of spaced, transverse upper and lower beams 16, 18 and a pair of opposing upper and lower carriages 20, 22 which move back and forth along the beams 16, 18 in the cross-direction, that is the direction indicated by the arrows 29. The upper carriage 20 carries an upper head 24 of the caliper gauge 10, while the lower carriage 22 carries a lower head 26. The two carriages 20, 22, and thus the two caliper heads 24, 26 are juxtaposed to provide a gap through which the sheet 14 freely moves in the machine direction, that is, the direction shown by arrow 28.

Although FIG. 1 shows only the caliper gauge 10 used to measure paper thickness, the carriages 20, 22 would typically also carry additional devices for measuring other physical properties of the sheet 14.

Figure 2:
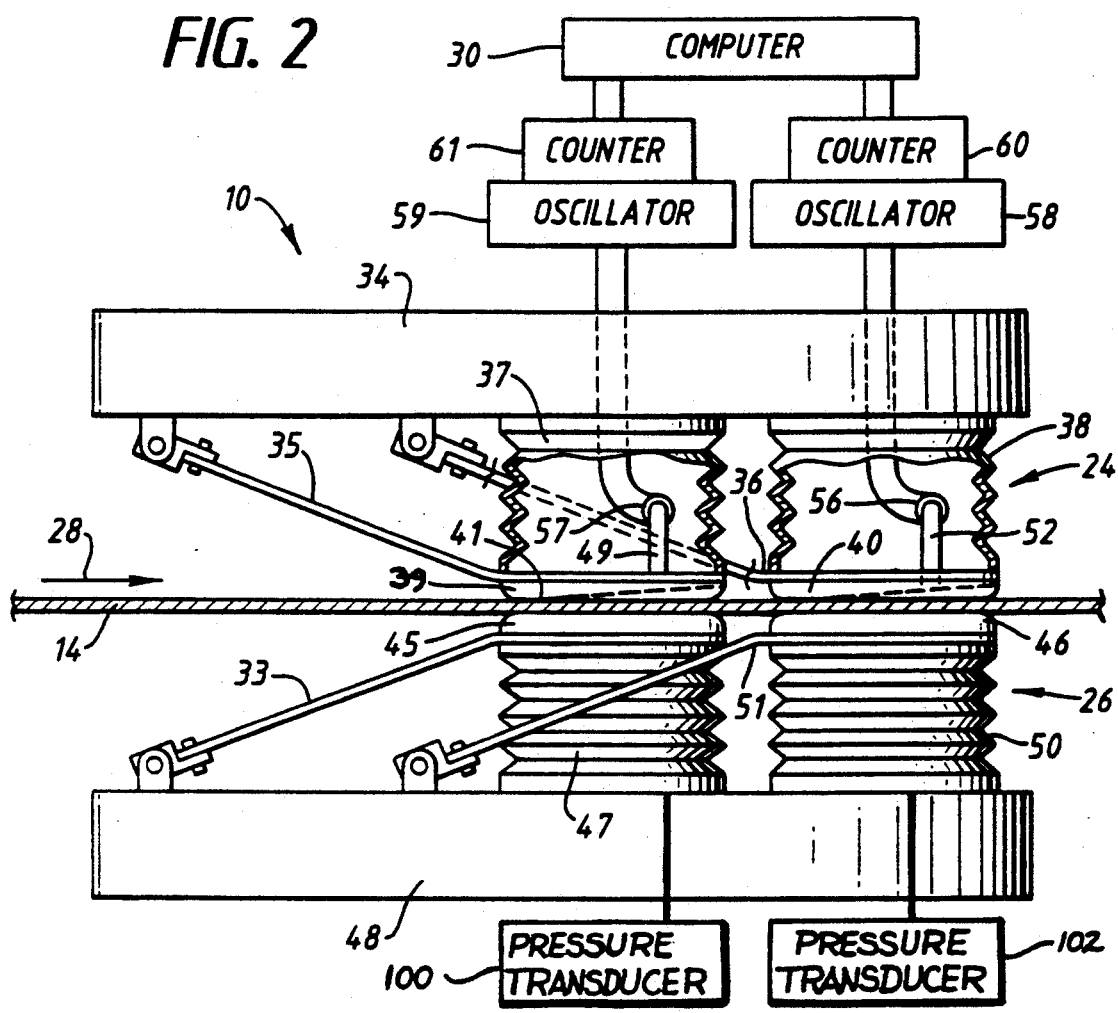
FIG. 2 is a schematic side elevation view, partly in cross-section, of one embodiment of the caliper gauge of the present invention.

FIG. 2 illustrates, in partial cross-section, the upper and lower heads 24, 26 of the caliper gauge 10. The sheet 14 moves rapidly between the upper and lower heads 24, 26 in the machine direction, that is, the direction shown by arrow 28. Thus, the sheet 14 moves from the front to the rear of the caliper gauge 10.

The upper head 24 of the caliper gauge 10 includes a sturdy, relatively massive base 34 (also shown in FIG. 1). One end of a support arm 36 is hinged toward the front of base 34. The other end of the support arm 36 is connected to a bellows 38. The bellows 38 connects the other end of the support arm 36 to the base 34 near the back of the gauge 10. The bellows 38 is disposed substantially perpendicular to the sheet 14. A first sheet-contacting pad 40 is attached to the end of the bellows 38.

Figure 4:
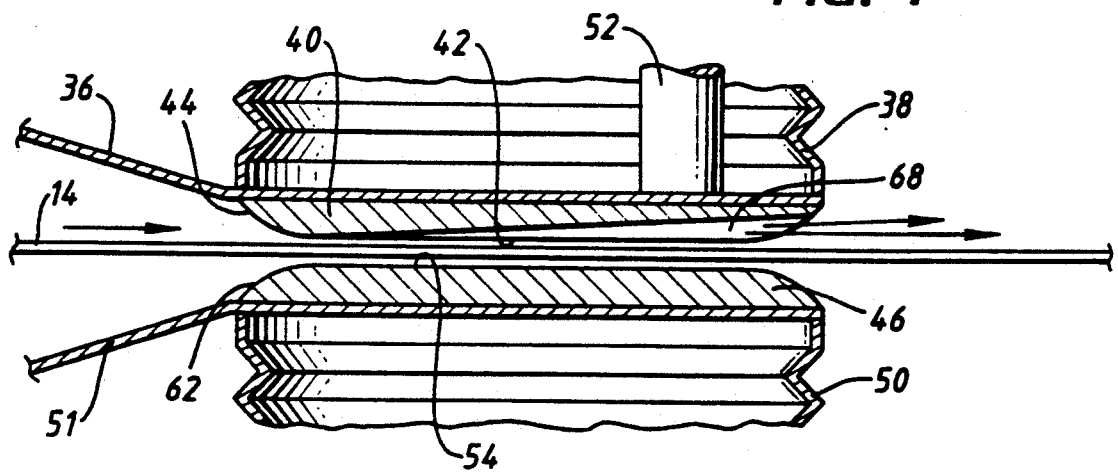
FIG. 4 is a side elevation view showing details of the caliper pads of FIG. 2.

As shown in FIG. 4, the first pad 40 has a sheet contacting surface 42 which is substantially parallel to the sheet 14. The pad 40 has a rounded portion 44 at the front to guide the paper 14 between the first pad 40 and a second pad 46. When pressurized, the bellows 38 forces the first pad 40 into contact with the upper surface of the sheet 14.

FIG. 4 also shows a second pad 46 opposing the first pad 40, having a sheet contact surface 54, being substantially parallel to the sheet 14 and having a rounded portion 62 at the front to guide the paper 14 between the first and second pad 40 and 46.

As shown in FIG. 2, the upper head 24 of the caliper gauge 10 also includes a support arm 35 hinged at one end to the front of base 34. The other end of the support arm 35 is attached to a bellows 37. The bellows 37 connects the other end of the support arm 35 to the base 34 near the center of the caliper gauge 10. The bellows 37 is disposed substantially perpendicular to the sheet 14. A third sheet-contacting pad 39 is attached to the end of the bellows 37.

As shown in FIG. 2, the third pad 39 is similar in construction to the first pad 40. The third pad 39 has a sheet-contacting surface 41 which is substantially parallel to the sheet 14 and a rounded portion at the front of the pad to guide the sheet 14 between the third pad 39 and a fourth pad 45. When pressurized, the bellows 37 forces the third pad 39 into contact with the upper surface of the sheet 14.

The lower head 26 is similar in construction to the upper head 24. Like the upper head 24, the lower head 26 includes a second sturdy, relatively massive base 48, a second sheet-contacting pad 46 connected to a bellows 50 and support arm 51. A fourth sheet-contacting pad 45 is connected to a bellows 47 and a support arm 33. Each of these elements is connected in substantially the same manner as that described above for the upper head 24, except, of course, the lower head 26 is mounted to the lower carriage 22.

Figure 3:
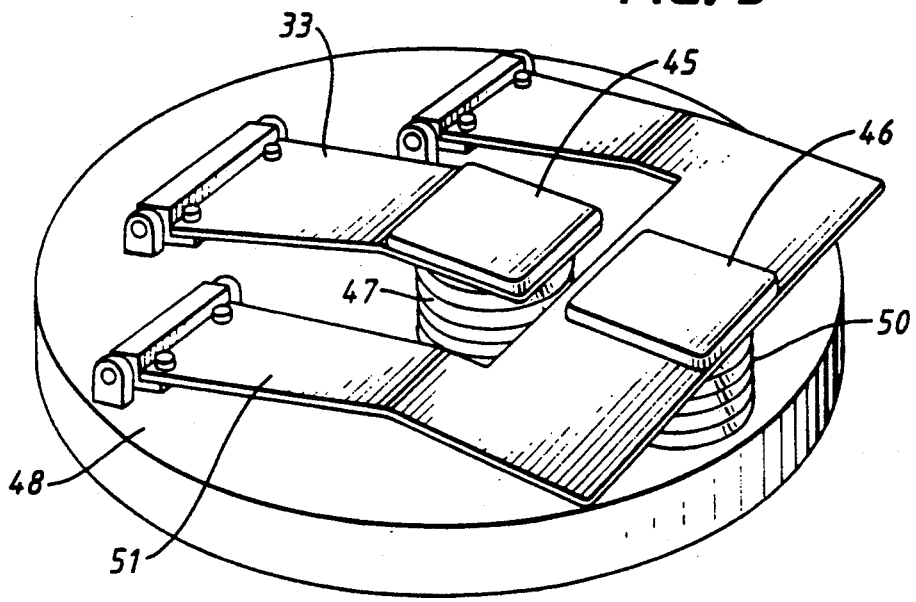
FIG. 3 illustrates, in perspective, an embodiment of the lower portion of the caliper gauge of FIG. 2.

FIG. 3 illustrates the relationship between the support arms 33, 51 which are hinged at their ends to the lower base 48. The other ends of the support arms are connected to both bellows 47, 50 as well as pads 45, 46, respectively.

As shown in FIG. 2, the upper and the lower heads 24, 26 are positioned such that the upper and lower bellows 38, 50 as well as the upper and lower bellows 37, 47 are in a substantially linear, opposing relationship. Thus, during operation of the caliper gauge 10, the first and second pads 40, 46 and the third and fourth pads 39, 45 are disposed in substantial opposing relationship on opposite sides of the sheet 14. The pads 45, 46 should be sufficiently broad in lateral extent so that slight lateral misalignments between the upper and lower heads 24, 26 will not induce a falsely large caliper measurement.

In general, any resiliently extendible means could be used in place of each bellows. However, a bellows is preferred because the electromagnetic circuit used to measure the thickness of the sheet material may be placed within the hollow interior of the bellows. One such circuit is fully described in the commonly assigned U.S. Pat. No. 3,828,248 to Gunnar Wennerberg which is incorporated herein by reference.

Figure 5:
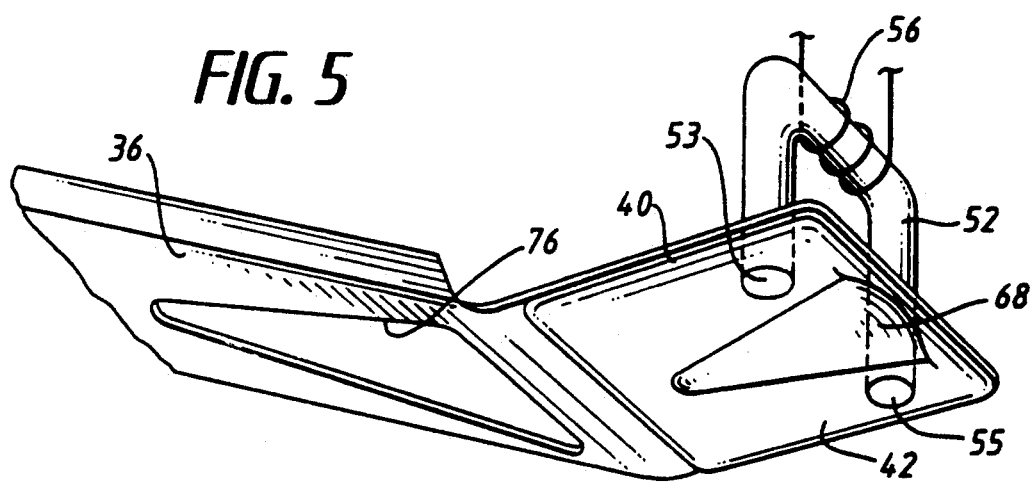
FIG. 5 illustrates, in perspective, an aerodynamically designed caliper pad, as shown in FIGS. 2 and 3, with an electromagnetic core straddling a vacuum notch and mounted toward the rear end of the caliper pad.

Briefly, however, the caliper gauge 10 is equipped with an electromagnetic proximity sensing device for accurately measuring the distance between the opposing pads. For example, as shown in FIGS. 4–5, with respect to the opposing pads 40, 46, the device includes an electromagnetic core 52 mounted to the first pad 40 and disposed within the upper bellows 38. The electromagnetic core 52 is disposed so that its two pole faces 53, 55 are mounted to that portion of the first pad 40 which remains in closest proximity with the sheet 14. When the first pad 40 has a vacuum notch 68, the electromagnetic core 52 is disposed so that its two pole faces 53, 55 are located in the rear half of the first pad 40. The two pole faces 53, 55 are preferably mounted transverse to the direction of sheet travel and straddle the vacuum notch 68. Favorable results have been obtained when the two pole faces 53, 55 are located near the rear edge of the first pad 40, where a pad 40, having a vacuum notch 68, remains closest to the sheet 14.

The first pad 40 is preferably formed of a highly abrasion resistant, non-magnetic material, such as sapphire. The second pad 46 is formed of a magnetically susceptible abrasion resistant material, such as ferrite, preferably coated with sapphire or diamond. The pads 40, 46 are preferably abrasion resistant to avoid excessive wear caused by the friction between the moving sheet 14 and the sheet contacting surfaces 42, 54 of the pads 40, 46. Pads 39, 45 are made of the same material and have the same construction (FIG. 2).

As shown in FIG. 2, the coil 56 surrounding the electromagnetic core 52 may be electrically connected to an oscillator circuit 58 and used as the inductance of that circuit. Thus, movement of the magnetically susceptible ferrite pad 46 toward and away from the coil 56 due to sheet thickness variations modifies the inductance of the coil 56 and hence the resonant frequency of the oscillator 58. A frequency counter 60 is operatively coupled to the oscillator 58 to determine its resonant frequency. The counter 60 then sends a signal to a computer 30 indicative of this resonant frequency. The computer 30 computes the distance between the pad 40 and the pad 46, and hence, sheet thickness based upon this resonant frequency.

The first pad 40 should also be abrasion resistant because, as shown in FIG. 5, the electromagnetic core 52 is preferably recessed within the pad 40 so that the pole faces 53, 55 are in close proximity to the sheet contacting surface 42 of the pad 40. The proximity sensing circuits are calibrated with the unworn pad. Therefore, if the sheet contacting surface 42 of the pad 40 is worn down, the pole faces 53, 55 of the electromagnetic core 52 will move closer to the sheet 14 and produce an erroneous thickness measurement or tear the sheet.

The support arm 36 shown in FIG. 5 is representative of the other support arms 33, 35, 51 and may be made of a lightweight material such as Mylar. The support arm 36 should preferably have a vent hole 76 to reduce the lifting effect of the air which moves along with the rapidly moving sheet 14.

The caliper gauge 10 is also equipped with a similar electromagnetic proximity sensing device for accurately measuring the distance between opposing pads 39, 45. As shown in FIG. 2, like the electromagnetic proximity sensing device for opposing pads 40, 46, the sensing device includes an electromagnetic core 49, a coil 57, an oscillator circuit 59 and a frequency counter 61. Each of these elements operates and is connected in the same manner as that described above for the sensing device for measuring the distance between opposing pads 40, 46.

As the caliper gauge 10 scans back and forth across the sheet 14, signals from the gauge 10 are sent via signal processing circuitry from the frequency counters 60, 61 to the computer 30. Because the opposing pads 39, 45 are directly upstream from pads 40, 46, both sets of pads detect the thickness of the sheet 14 at the same cross-directional location. The computer 30 manipulates the signals from the frequency counters 60, 61 so that caliper of the sheet 14 is measured at the same machine directional location. For example, the signal offset may be computed from the distance between opposing pads 40, 46 and opposing pads 39, 45 and the machine directional velocity of the sheet 14 or obtained by cross-correlation where the signals are shifted in relation to each other until their correlation is maximal.

In operation, the sheet 14 is threaded between the opposing caliper heads 24, 26 and the computer 30 instructs the scanning station 12 to begin scanning the caliper gauge 10 back and forth along the cross-direction of the sheet 14. The bellows 37, 47 are pressurized to place opposing pads 39, 45 in opposing contact with the sheet 14. A pressure $P_L$ of about 5 inches of water (gauge) in 1-inch diameter bellows will provide sufficient pressure to maintain the pads 39, 45 of FIG. 2 in contact or in close proximity (less than about two microns) to the sheet 14 over a relatively wide range of sheet speeds. Bellows 38, 50 are also pressurized to place pads 40, 46 in opposing contact with the sheet 14. A higher pressure $P_H$ of about 10–20 inches of water (gauge) in 1-inch diameter bellows will provide sufficient pressure to maintain the pads 40, 46 of FIG. 2 in contact with the sheet 14 over a relatively wide range of sheet speeds.

Simultaneously, when the caliper is measured, a pressure transducer 100 sends signals indicative of the pressure $P_L$ in bellows 37, 47 to an analog-to-digital converter (not shown). The digitized signals are then sent to the computer 30. Similarly, a second pressure transducer 102, sends signals indicative of the pressure $P_H$ in bellows 38, 50 to the analog-to-digital converter (not shown), then the digitized signals are sent to a computer 30. Through cross-correlation of the signals described earlier, the sheet caliper measurements $C_H$ and $C_L$, at pressures $P_H$ and $P_L$, respectively, are measured at the same location of sheet 14.

Figure 6:
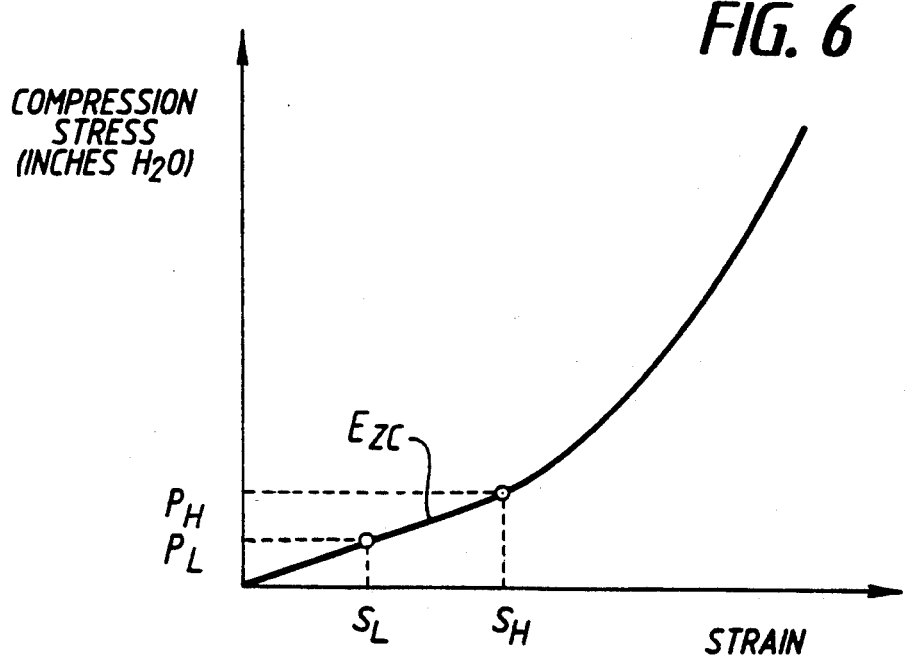
FIG. 6 a stress-strain diagram derived from measuring the compressibility of a sheet subjected to a plurality of pressures.

The resulting data can be stored in computer 30 to generate a compression stress-strain diagram (FIG. 6). The ordinate of the diagram is the stress exerted by the pads upon the sheet, which is proportional to the bellow's pressure. The higher pressure of bellows 38, 50 is still set low enough so that the compressibility data is within the linear region of the stress-strain curve. The abscissa of the diagram is the strain exerted on the sheet. The strain is defined as the caliper reduction resulting from the increase in pressure of bellows 38, 50 to that of bellows 37, 47 divided by the caliper of the paper at the lower pressure in bellows 37, 47. From this data, a Z-directional compression modulus of elasticity $E_{ZC}$ may defined by the following formula:

$$E_{ZC} = \frac{\Delta \text{ stress}}{\Delta \text{ strain}} = \frac{\text{pressure increase}}{\left(\frac{\text{caliper reduction}}{\text{initial caliper}}\right)} = \frac{P_H - P_L}{\left(\frac{C_L - C_H}{C_L}\right)}$$

Where $E_{ZC}$ = the Z-directional compression modulus of elasticity.

A Z-directional tensile modulus of elasticity $E_{ZT}$ may be computed from the Z-directional compression modulus of elasticity $E_{ZC}$ for various grades of paper as follows:

$$E_{ZT} = k \cdot E_{ZC}$$

Where k is an experimental constant

The tensile modulus of elasticity $E_{ZT}$ can be then used to empirically derive various Z-directional properties of the paper, such as the Z-directional tensile strength as follows:

$$S_{ZT} = A \cdot E_{ZT}^B + C \cdot W^D \cdot C_L^E + F \cdot V^G$$

Where
$S_{ZT}$ is Z-directional tensile strength;
$E_{ZT}$ is the Z-directional tensile modulus of elasticity;
W is the basis weight of sheet 14;
$C_L$ is the caliper of the sheet 14 subjected to the lower pressure $P_L$ of bellows 37, 47;
V is velocity of the sheet 14 passing through the caliper gauge 10; and
A, B, C, D, E, F and G are experimentally determined constants.

Scott bonding can be computed by a similar formula with a different set of constants as follows:

$$S_B = H \cdot E_{ZT}^I + J \cdot W^K \cdot C_L^L + M \cdot V^N$$

Where
$S_B$ is the Scott bonding value; and
H, I, J, K, L, M and N are experimentally determined constants.

Extensional stiffness can be computed by a similar formula with another set of constants as follows:

$$X_Z = O \cdot E_{ZT}^P + Q \cdot W^R \cdot C_L^T + U \cdot V^Y$$

Where
$X_Z$ is the extensional stiffness of the sheet 14; and
O, P, Q, R, T, U and Y are experimentally determined constants.

The above equations are applicable to a wide variety of papers being manufactured. The constants A, B, C, D, E, F, G, H, I, J, K, L, M, N, O, P, Q, R, T, U and Y vary depending on the particular paper being made, and on which test is being simulated. The constants for a given papermaking system can be determined by measuring the various parameters (e.g., velocity of the sheet 14 and basis weight, etc.) of the system during production and analyzing the above formulas with a linear regression program.

A preferred embodiment of the present invention has been described. Nevertheless, it will be understood that various modifications may be made without departing from the spirit and scope of the invention, as determined by the appended claims.

We claim:

1. A sensor for use in determining sheet caliper measured at a plurality of pressures exerted on the sheet, the sheet having opposed, first and second major surfaces, the sensor comprising:
   means for simultaneously pressing the first and second major surfaces on opposite sides of the sheet at a plurality of pressures;
   means for measuring and generating a signal indicative of said plurality of pressures; and
   means for measuring and generating a signal indicative of sheet caliper at the plurality of pressures.

2. The sensor of claim 1, wherein the pressing means presses the sheet at spaced apart locations.

3. The sensor of claim 2, wherein the sheet travels in a machine direction and the spaced apart locations lie on a line in the machine direction.

4. A system for determining a physical property of a traveling sheet, said physical property being a function of sheet caliper measured at a plurality of pressures exerted on the sheet, the sheet having opposed, first and second major surfaces, the system comprising:
   a first sheet-contacting pad disposed adjacent to the first major surface;
   a second sheet-contacting pad opposing the first pad and disposed adjacent to the second major surface;
   a third sheet-contacting pad disposed upstream from the first pad adjacent to the first major surface;
   a fourth sheet-contacting pad opposing the third pad and disposed adjacent to the second major surface;
   means, operatively coupled to the first pad, for measuring and generating a signal indicative of the distance between the first and second pads;
   means, operatively coupled to the third pad, for measuring and generating a signal indicative of the distance between the third and fourth pads;
   means for pressing the first and second pads toward the sheet at a first predetermined pressure and for pressing the third and fourth pads toward the sheet at a second predetermined pressure and for generating signals indicative of said first and second pressures, wherein the first predetermined pressure is different than the second predetermined pressure; and
   a computer responsive to said generated signals for determining the caliper of said sheet and said physical property.

5. The system of claim 4, wherein the first predetermined pressure is greater than the second predetermined pressure.

6. The system of claim 4, further comprising means for comparing the sheet caliper measured at the plurality of pressures with one another.

7. The system of claim 4, further comprising means for comparing the plurality of pressures with one another.

8. The system of claim 4, in which said computer determines the compression modulus of elasticity based on the plurality of pressure and sheet caliper measurements.

9. The system of claim 4, in which the computer determines the z-directional tensile strength of the sheet based upon the plurality of pressure and caliper measurements.

10. The system of claim 4, in which the computer determines the Scott bonding of the sheet based upon the plurality of pressure and caliper measurements.

11. The system of claim 4, in which the computer determines the extensional stiffness of the sheet based upon the plurality of pressure and caliper measurements.

12. The system of claim 4, wherein the sheet is paper.

13. The system of claim 4, wherein the pressing means includes bellows for pressing the sheet at least at two different locations.

14. The system of claim 13, wherein the two different locations lie on a line parallel to the machine direction.

15. A method for determining a physical property of a sheet, said physical property being a function of sheet caliper measured at a plurality of pressures exerted on the sheet, the sheet having opposed, first and second major surfaces, the method comprising the steps of:
   pressing the first and second major surfaces on opposite sides of the sheet at a plurality of pressures;
   measuring the plurality of pressures;
   measuring the sheet caliper at the plurality of pressures; and
   computing the physical property based upon the pressure and caliper measurements.

16. The method of claim 15, further comprising the step of comparing the measurements of sheet caliper at the plurality of pressures.

17. The method of claim 15, further comprising the step of computing the compression modulus of elasticity based on the measurements of sheet caliper and pressure.

18. The method of claim 15 further comprising the step of computing the tensile modulus of elasticity based on the measurements of sheet caliper and pressure.

19. The method of claim 15, further comprising the step of computing the Z-directional tensile strength based on the measurements of sheet caliper and pressure.

20. The method of claim 15, further comprising the step of computing the Scott bonding based on the measurements of sheet caliper and pressure.

21. The method of claim 15, further comprising the step of computing the extensional stiffness based on the measurements of sheet caliper and pressure.

22. A system for determining a z-directional physical property of a sheet having a sheet caliper and opposed, first and second major surfaces, the system comprising:
   means for pressing the first and second major surfaces on opposite sides of the sheet at a plurality of pressures;
   means for measuring the plurality of pressures;
   means for measuring the sheet caliper at said plurality of pressures; and
   means for computing the physical property based on the pressure and sheet caliper measurements.

23. A system, as defined in claim 22, in which:
   the physical property is the compression modulus of elasticity of the sheet.

24. A system, as defined in claim 22, in which:
   the physical property is z-directional tensile strength of the sheet.

25. A system, as defined in claim 22, in which:
   the physical property is the Scott bonding of the sheet.

26. A system, as defined claim 22, in which:
   the physical property is the extensional stiffness of the sheet.

27. A system, as defined in claim 22, in which:
the pressing means presses the sheet at spaced apart locations.

28. A system, as defined in claim 27, in which:
the computing means includes means for comparing the pressures and the sheet calipers measured at the spaced apart locations.

29. A system, as defined in claim 27, in which:
the sheet travels in a machine direction and the spaced apart locations lie on a line in the machine direction.

30. A sensor for use in determining the caliper of a sheet, the sensor comprising:
means for compressing the sheet in a z-direction at a first pressure at a first location relative to the traveling sheet;
means for compressing the sheet in the z-direction at a second pressure at a second location relative to the traveling sheet, the second pressure being different than the first pressure;
means for measuring the first and second pressures and generating signals indicative thereof; and
means for measuring the sheet caliper at the first and second locations and generating signals indicative thereof.

31. A sensor, as defined in claim 30, in which:
the first and second locations are spaced apart along the machine direction of the traveling sheet.

32. A method for determining a z-directional physical property of a sheet traveling in a machine direction, the method comprising the steps of:
compressing the sheet in the z-direction at a first location along the machine direction using a first pressure;
measuring the first pressure;
measuring the caliper of the compressed sheet at said first location;
compressing the sheet in the z-direction at a second location in substantial alignment with the first location along the machine direction using a second pressure, the second pressure being different than the first pressure;
measuring the second pressure;
measuring the caliper of the compressed sheet at the second location; and
calculating the physical property based on the pressure and caliper measurements.

* * * * *